United States Patent [19]

Mautner et al.

[11] Patent Number: 5,476,958
[45] Date of Patent: Dec. 19, 1995

[54] PROCESS FOR THE REMOVAL OF OLEFINS FROM SILANES

[75] Inventors: Konrad Mautner, Kastl; Anton Schinabeck, Burghausen, both of Germany

[73] Assignee: Wacker-Chemie GmbH, Munich, Germany

[21] Appl. No.: 418,218

[22] Filed: Apr. 6, 1995

[30]  Foreign Application Priority Data

May 5, 1994 [DE] Germany .................... 44 15 924.2

[51] Int. Cl.⁶ ................................................. C07F 7/08
[52] U.S. Cl. ..................................................... 556/466
[58] Field of Search .................................... 556/466

[56] References Cited

U.S. PATENT DOCUMENTS 4,740,607  4/1988  Bokerman et al. ............... 556/466
5,210,250  5/1993  Watanuki et al. .................. 556/466

FOREIGN PATENT DOCUMENTS 0310258  4/1989  European Pat. Off. .

*Primary Examiner*—Paul F. Shaver
*Attorney, Agent, or Firm*—Martin Connaughton

[57] ABSTRACT

In the process for the removal of olefins from the silanes or silane mixtures obtained during methylchlorosilane synthesis, the olefins are reacted with hydrogen in the presence of hydrogenation catalysts.

3 Claims, No Drawings

PROCESS FOR THE REMOVAL OF OLEFINS FROM SILANES

FIELD OF INVENTION

The present invention relates to a process for the removal of olefins from silanes and silane mixtures obtained in the direct synthesis of methylchlorosilanes.

BACKGROUND OF INVENTION

Olefins, like saturated hydrocarbons, aromatics and chlorohydrocarbons, are by-products in the direct synthesis of methylchlorosilanes by the Müller-Rochow method from silicon and chloromethane at 250° to 300° C. using copper catalysts. In contrast to alkanes, olefins are reactive due to their carbon-carbon double bond and can lead to impairment in a number of subsequent processes. For example, they are capable of adding on HCl which is eliminated when exposed to heat. The HCl split off can lead to inhibition of catalysts, to corrosion of containers and plant, and to acid-catalyzed side reactions in processes or at places where participation of HCl should actually be excluded. Olefins themselves may also have an inhibiting action, for example on noble metal catalysts during hydrosilylation.

Attempts have been made to remove olefins as far as possible by distillation. However, the boiling points are often so close to the boiling points of monomeric organochlorosilanes that removal cannot be carried out with an acceptable expenditure.

EP-A 310 258 describes a process for reducing the content of olefins in methylchlorosilanes in which the olefins are reacted with methylchlorosilanes containing hydrogen atoms bonded directly to silicon (H-silanes) in the presence of a dissolved platinum catalyst to give silaalkanes. For a complete conversion, the process requires H-silanes in excess, which, if they have been added additionally to the original silane stream also have to be removed again. The silaalkanes must also be removed, since they usually contain reactive groups, such as Si—Cl.

There was the object of providing a process for the removal of olefins from the silanes or silane mixtures obtained during methylchlorosilane synthesis, in which only substances which can easily be removed are introduced into the silanes or silane mixtures.

SUMMARY OF INVENTION

The present invention relates to a process for the removal of olefins from the silanes or silane mixtures obtained during methylchlorosilane synthesis, the olefins being reacted with hydrogen in the presence of hydrogenation catalysts.

The olefins are converted into the corresponding alkanes. For examples, 3-methylpentane is formed from 3-methyl-2-pentene. Because of their slow reaction and their quite low concentration, the alkanes can remain in the silanes or silane mixtures. If the alkanes have to be removed, however, this can be done by simple distillation.

At least one mole of hydrogen is employed per mole of double bonds in the olefins. Hydrogen is preferably used in an excess of at least 2 mole per mole of double bonds. Since hydrogen is present as a gas at the temperatures and pressures in question, it can be removed easily from the silanes or silane mixtures after the reaction. Commercially available hydrogen can be employed for hydrogenation purposes. Preferably, the hydrogen is dispersed as finely as possible in the silane or silane mixture upstream of the catalyst bed.

The term "silanes or silane mixtures obtained during methylchlorosilane synthesis" also comprises silanes or silane mixtures separated off, concentrated or further processed after the synthesis, and also includes phenylchlorosilanes.

The silanes or silane mixtures obtained during methylchlorosilane synthesis generally comprise silanes of the formula $$R_xCl_{3-x}Si\text{-}[SiR_yCl_{2-y}]_n\text{-}A \qquad (I)$$

in which

R is a hydrogen atom or a methyl, phenyl or ethyl radical,

A is a chlorine atom or a radical R, x is 0, 1, 2 or 3, y is 0, 1, 2 and n is 0 or 1.

Examples of the silanes of formula I are methylchlorosilanes, such as methyltrichlorosilane, methyldichlorosilane, dimethyldichlorosilane, trimethylchlorosilane, trimethylsilane and tetramethylsilane; ethylchlorosilanes, such as ethyltrichlorosilane; phenylchlorosilanes, such as phenyltrichlorosilane and phenylmethyldichlorosilane; chlorosilanes, such as trichlorosilane and tetrachlorosilane; and oligosilanes, such as hexachlorodisilane, hexamethyldisilane and methylchlorodisilanes. Preferably, the silane mixture comprises no H-silanes or oligosilanes.

The olefins to be removed are linear or branched olefins having 2 to 10 carbon atoms. The olefins which cause interference have 5 to 7 carbon atoms, boil at between 20° and 100° C. and can occur in various regio- and stereochemical isomers, for example isomeric methylbutenes, isomeric 2,3-dimethylbutenes, 2,3,3-tri-methyl-1-butene, isomeric methylpentenes, isomeric dimethylpentenes, isomeric hexenes, isomeric methylhexenes and isomeric heptenes.

The content of olefins in industrial silanes, silane mixtures and silane streams of the large-scale industrial distillation of silanes depends on the silane or silane mixture in question and on the state of the silane synthesis. By-products occur to an increased extent at the start-up phase and in the run-down phase of silane reactors. Olefin contents up to 10,000 ppm can therefore occur.

Linear and branched alkanes having 1 to 10 carbon atoms, chlorohydrocarbons having 1 to 10 carbon atoms and 1 to 3 chlorine atoms and aromatic hydrocarbons having 6 to 10 carbon atoms often occur as further impurities of the silanes or silane mixtures.

Suitable catalysts are all the known hydrogenation catalysts. Hydrogenation catalysts are classified in homogeneous and heterogeneous catalysts.

Homogeneous hydrogenation catalysts are complex compounds of transition metals, in particular metals of the 8th sub-group. A more preferred example is $(Ph_3P)_3RuCl$, also known as Wilkinson's catalyst.

A number of transition metals, transition metal oxides and transition metal sulfides in finely divided form act as heterogeneous hydrogenation catalysts. The transition metals are preferably metals of sub-group 1, 2, 6 and 8, such as copper, zinc, chromium, iron, nickel, cobalt, rhodium, ruthenium, platinum and palladium. Examples of suitable oxides are copper chromite $(CuO.Cr_2O_3)$ and zinc chromite $(ZnO.Cr_2O_3)$. Examples of suitable sulfides are molybdenum sulfide and tungsten sulfide.

Heterogeneous hydrogenation catalysts, specifically transition metals of sub-group 8, for example iron, nickel, cobalt, rhodium, ruthenium, platinum and palladium, more preferably palladium and platinum, are employed.

Preferably, the heterogeneous hydrogenation catalysts are applied to supports, so that they can be employed, for example, in a fixed bed reactor through which the mixture flows, such as a distillation column or a flow-through reactor.

The supports are preferably in piece form in order to keep the drop in pressure as the silanes or silane mixtures flow through as low as possible. Possible support materials are all the customary materials, such as charcoal and ceramic supports. Examples of supports are active charcoal and inorganic oxides, such as silicon dioxide, aluminum(III) oxide, silicates, titanium dioxide and zirconium dioxide; and carbides, such as silicon carbide; active charcoal and silicon dioxide being preferred examples. Palladium on active charcoal in pieces is more preferred as the hydrogenation catalyst.

Such hydrogenation catalysts, in which the finely divided metals are on supports, can be prepared by reduction of metal compounds in the presence of the support.

The concentration of the metals on the supports is preferably 0.5% to 5% by weight, based on the total weight of the catalyst; however, higher or lower concentrations can also be used.

The catalyst used can be employed in the liquid phase or in the gas phase.

To maintain the activity of the catalyst for as long as possible, the silanes or silane mixtures should be free from solid or pasty impurities and should comprise no heavy metals, such as lead, which act as catalyst poisons. The troublesome impurities mentioned can be removed by simple distillation.

The hydrogenation takes place at room temperature, about 20° C., and ambient pressure, about 0.10 MPa. As the temperature rises, the hydrogenation result also improves, i.e., the residence time for >95% removal drops. Preferred temperatures are 20° to 90° C., in particular 40° to 80° C. The upper limit of the temperature is determined by the boiling point of the mixture. The hydrogenation can be carried out under various pressures. Preferred pressures are 0.1 to 0.5 MPa, in particular 0.1 to 0.3 MPa.

The residence time in the reactor, which is preferably operated continuously, extends from 1 second to 1 hour. The residence time is preferably less than 10 minutes.

The process can be carried out batchwise, semi-continuously or completely continuously, the completely continuous procedure preferably being employed.

EXAMPLE

The example in the table below shows, in addition to the influence of the temperature, the removal of olefins and the increase in alkanes. Olefin-containing methyltrichlorosilane was passed at various temperatures under 0.10 MPa through a vertical reactor of 50 mm diameter and 500 mm length, packed with a metallic palladium catalyst on active charcoal in pieces (5% by weight of Pd, obtainable under the designation K-0219 from W. C. Heräus GmbH, Hanau), from the bottom. Hydrogen was fed in co-current in the catalyst bed. The residence time was 5 minutes and the volume flow of hydrogen was 1.3 liter/hour.

TABLE

| Hydrogenation of olefins in methyltrichlorosilane | | | | |
|---|---|---|---|---|
| | 20° C. | | 50° C. | |
| Components | before reactor [ppm] | after reactor [ppm] | before reactor [ppm] | after reactor [ppm] |
| trans-2-hexene | 15 | 1 | 15 | 0 |
| cis-3-methyl-2-pentene | 18 | 1 | 18 | 0 |
| cis-2-hexene | 25 | 0 | 25 | 0 |
| trans-3-methyl-2-pentene | 6 | 1 | 6 | 0 |
| 2,3-dimethyl-2-butene | 14 | 6 | 14 | 1 |
| 2-methylpentane | 0 | 5 | 0 | 15 |
| 3-methylpentane | 0 | 11 | 1 | 47 |

What is claimed is:

1. A process for the removal of olefins from silanes or silane mixtures obtained during methylchlorosilane synthesis, comprising reacting the olefins in the silanes or silane mixture with hydrogen in the presence of a hydrogenation catalyst.

2. The process as claimed in claim 1, wherein the olefins to be removed are linear or branched olefins having 2 to 10 carbon atoms.

3. The process as claimed in claim 1, wherein the hydrogenation catalyst is selected from the group consisting of iron, nickel, cobalt, rhodium, ruthenium, platinum and palladium.

\* \* \* \* \*